United States Patent [19]

Ochiai et al.

[11] Patent Number: 4,595,537

[45] Date of Patent: Jun. 17, 1986

[54] POLYGLYCEROL COMPOUNDS AND COSMETIC PRODUCTS CONTAINING THE SAME

[75] Inventors: Michio Ochiai; Hiromichi Sagitani, both of Kanagawa, Japan

[73] Assignee: Pola Chemical Industries, Inc., Japan

[21] Appl. No.: 750,231

[22] Filed: Jun. 28, 1985

Related U.S. Application Data

[63] Continuation of Ser. No. 481,322, Mar. 31, 1983, abandoned.

[30] Foreign Application Priority Data

Apr. 13, 1982 [JP] Japan ................................. 57-61264

[51] Int. Cl.[4] ........................ C07C 43/10; C07C 43/14
[52] U.S. Cl. ............................... 260/410.6; 260/410.7; 568/616; 568/624; 568/617; 514/772

[58] Field of Search ............... 568/616, 617, 623, 624; 260/410.6, 410.7

[56] References Cited

U.S. PATENT DOCUMENTS 3,595,924  7/1971  Kalopissis et al. .
3,846,546  11/1974  Lachampt et al. .
4,329,445  5/1982  Del Pesco .

FOREIGN PATENT DOCUMENTS 707486  6/1968  Belgium .

Primary Examiner—Howard T. Mars
Attorney, Agent, or Firm—Irvin A. Lavine

[57] ABSTRACT

A novel randomly polymerized polyglycerol, polytrimethylene- or -tetramethylene-oxide condensate of an 8–36 carbon aliphatic alcohol or fatty acid useful as a non-ionic surface active agent.

4 Claims, 8 Drawing Figures

POLYGLYCEROL COMPOUNDS AND COSMETIC PRODUCTS CONTAINING THE SAME

This application is a continuation of application Ser. No. 481,322, filed 3/31/83.

FIELD OF THE INVENTION

The present invention relates to a novel polyglycerol compound useful as a nonionic surface active agent or surfactant and a cosmetic product containing it.

BACKGROUND OF THE INVENTION

The nonionic surfactants known in the art and used widely include glycerol fatty acid esters, sorbitan fatty acid esters, poly(oxyethylene)sorbitan fatty acid esters, poly(oxyethylene) fatty acid esters, poly(oxyethylene)alkyl ethers, poly(oxyethylene)alkyl phenyl ethers, hydrogenated castor oil poly(oxyethylene) adducts and the like. These surfactants are generally broken down into lipophilic and hydrophilic types, the former having no poly(oxyethylene) chain or a short poly(oxyethylene) chain and the latter having a long poly(oxyethylene) chain. A surfactant mixture containing a higher proportion of hydrophilic surfactants provides a oil-in-water (O/W) type emulsion having its hydrophilic-lipophilic balance (HLB) adjusted to 10–15, while a surfactant mixture containing a higher proportion of hydrophilic surfactants provides a water-in-oil (W/O) type emulsion having its HLB adjusted to 4–6. Thus sophisticated adjustment of the hydrophilic-lipophilic balance is required for the preparation of stable emulsions. With the nonionic surface active agents, that adjustment is performed making use of the poly(oxyethylene) chain. This is because the control of the chain length of ethylene oxide is easy and can meet sufficiently the requirement on sophisticated HLB. However, the surfactants to which ethylene oxide is added have some disadvantages in that dioxane forms during synthesis, they suffer oxidation with the lapse of time so that elution of formaldehyde takes place and their pH shifts toward acidity. These problems may be solved by the addition of antioxidants; however, the use of such antioxidants is unpreferable in view of safety.

On the other hand, the nonionic surfactants known in the art and used extensively as solubilizers include poly(oxyethylene)octyl phenyl ether, poly(oxyethylene)nonyl phenyl ether, poly(oxyethylene)oleyl ether, poly(oxyethylene)monolaurate, poly(oxyethylene)monooleate, hydrogenated castor oil poly(oxyethylene) adducts, poly(oxypropylene)poly(oxyethylene)cetyl ether, poly(oxyethylene)2-hexyldecyl ether and the like. All of these solubilizers are Micelle-dissolved in water, and are so adjusted that the resulting aqueous solutions are put into a relatively hydrophilic state having a HLB of not less than 12 so as to solubilize oily matters, perfumes, oil-soluble matters, etc. To this end, ethylene oxide is unexceptionally added to the solubilizers. Like the foregoing emsulsifiers, however, the aqueous solution of surfactants to which ethylene oxide is added causes elution of formaldehyde and its pH shifts toward acidity, since the chain of ethylene oxide undergoes oxidation with the lapse of time. To this end, antioxidants or buffer solutions are added for pH adjustment. However, there is an increasing demand for solubilizers substantially in sensitive to oxidation in view of both safety and the stability of products. To add to this, the conventional solubilizers generally have so long a defoaming time that, when they are applied over the inside of a container or the skin, there are still some bubbles remaining on the surface thereof, which pose problems in connection with appearance and touch.

The aforesaid emulsifiers and solubilizers share a common problem. Antiseptics now used with cosmetic include paraben compounds such as methylparaben, which are known to be adsorbed onto the ethylene oxide moieties of surfactants and hence less effective.

U.S. Pat. No. 3,846,546, West German Pat. No. 1 719 434 and French Pat. No. 1 553 145 specifications disclose emulsifiers that are related to compounds of the present invention. However, since these known emulsifiers are of the branched structure that 1, 2 bonding is present in the alkylene oxide group, the following disadvantages are found from the standpoint of synthesis; (1) an alcohol used as a starting material remains unreacted, (2) the distribution of molecular weight is wide, (3) an addition reaction does not proceed so that difficulties are encountered in making them hydrophilic, (4) the content of polyglycerol unbonded to the starting alcohol is high, etc. In view of their physical properties, the known emulsifiers are also disadvantageous in that they are poor in solubility in water and dispersibility in O/W emulsions so that they do not function as good solubilizers and emulsifiers for O/W emulsions. This holds for even the compounds of these emulsifiers having an increased number of moles of hydrophilic groups present.

SUMMARY OF THE INVENTION

As a consequence of intensive studies made to eliminate the defects of the prior art, a novel nonionic surface active agent has been found, which is very easy to synthesize, excels in emulsifiability and solubility because of the straight-chain carbon skeletons of the polymethylene oxide groups, undergoes substantially neither elution of formaldehyde nor pH changes, has an improved resistance to oxidation, a reduced defoaming time in a soluble system and no stimulating effect on the skin, and is safe and stable. The present invention is also concerned with a cosmetic product in which the novel surfactant is applied as an emulsifier or solubilizer.

A main object of the present invention is therefore to provide a novel nonionic surfactant, polyglycerol compound having the following general formula (I) or (II):

$$R_1O(X_1)_{m_1}-Y_1-_{n_1}H \quad (I)$$

wherein $R_1$ is a straight-chain or branched, saturated or unsaturated aliphatic alcohol residue having carbon atoms of 8–36, $X_1$ is $CH_2CH_2CH_2O$ and/or $CH_2CH_2CH_2CH_2O$, $Y_1$ is a glycerol group, $m_1$ equals 3–60, and $n_1$ equals 4–60, or

$$R_2COO(X_2)_{m_2}-Y_2-_{n_2}H \quad (II)$$

wherein $R_2$ is a straight-chain or branched, saturated or unsaturated fatty acid residue having carbon atoms of 7–35, $X_2$ is $CH_2CH_2CH_2O$ and/or $CH_2CH_2CH_2CH_2O$, $Y_2$ is a glycerol group, $m_2$ equals 3–60, and $n_2$ equals 4–60.

Another object of the present invention is to provide a hydrophilic cosmetic product (O/W, solublized, water-dispersed) containing at least one or two or more of the polyglycerol compounds expressed by the general formula (I) or (II):

$$R_1O(X_1)_{m_1}-Y_{1-n_1}H \quad (I)$$

wherein $R_1$ is a straight-chain or branched, saturated or unsaturated aliphatic alcohol residue having carbon atoms of 8–36, $X_1$ is $CH_2CH_2CH_2O$ and/or $CH_2CH_2CH_2CH_2O$, $Y_1$ is glycerol group, $m_1$ equals 3–60, and $n_1$ equals 4–60, or $$R_2COO(X_2)_{m_2}-Y_{2-n_2}H \quad (II)$$

wherein $R_2$ is a straight-chain or branched, saturated or unsaturated fatty acid residue having carbon atoms of 7–35, $X_2$ is $CH_2CH_2CH_2O$ and/or $CH_2CH_2CH_2CH_2O$, $Y_2$ is a glycerol group, $m_2$ equals 3–60, and $n_2$ equals 4–60.

BRIEF DESCRIPTION OF THE DRAWINGS

The above-mentioned and other objects and features of the present invention will become apparent from the following detailed description with reference to the accompanying drawings, in which.

DETAILED DESCRIPTION OF THE INVENTION

Figure 1:
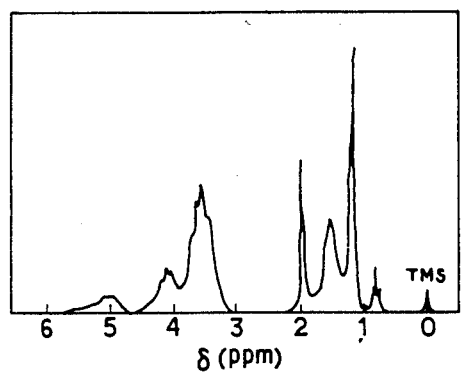
FIGS. 1, 2 and 3 are NMR charts of the compound after acetylation of poly(glycerol)(10)poly(1,4-oxybutylene)(9)2-octyldodecyl ether, poly(glycerol)(16)poly(1,4-oxybutylene)(12)stearyl ether and poly(glycerol)(32)poly(1,4-oxybutylene)(32)oleyl ether.

Reference will now be made to the structure of the polyglycerol compounds according to the present invention. The inventive compounds expressed by both the formulae (I) and (II) are those of higher saturated-unsaturated alcohols having a straight or branched chain and carbon atoms 8–36 or higher saturated unsaturated fatty acids having a straight or branched chain and carbon atoms of 8–36 to which added are 7–120 moles of trimethylene oxide and/or tetrahydrofuran and glycidol in total, wherein polyglycerol compounds are at random polymerized with glycidol and trimethylene oxide and/or tetramethylene oxide. A Proportion of glycerol group and polymethylen oxido groups is 95:5–1:3.

In formula (I), $m_1$ and $n_1$ are in a range of 3–60 and 4–60, respectively, but preference is given to $m_1$ in a range of 4–30 and $n_1$ in a range of 5–30. When both $m_1$ and $n_1$ exceed 60 in formula (I), any desired surfactant having an emulsifying or solubilizing effect is not obtained since there is then a drop of nonionic surface activity. It is noted that the degree of surface activity attained in a range of above 30 to below 60 is relatively low. When $R_1$ in formula (I) is a straight-chain aliphatic aloohol, the resulting surfactant is preferably used as an emulsifier, and when $R_1$ is a branched aliphatic alcohol, the resulting surfactant is preferably used as a solubilizer.

In formula (II), $m_2$ and $n_2$ are in a range of 3–60 and 4–60, respectively, but preference is also given to $m_2$ of 4–30 and $n_2$ 5–30. As explained with reference to formula (I), there is a lowering of surface activity, when both $m_2$ and $n_2$ exceed 60. As a result, any desired surfactant having the contemplated emulsifying and solubilizing effects is not obtained at all.

It is understood that $m_1/n_1$ and $m_2/n_2$ shall not exceed 3 in both formulae (I) and (II) from a viewpoint of surface activity.

The straight-chain or branched, higher saturated or unsaturated aliphatic alcohols used for the the polyglycerol ether type compounds expressed by formula (I) may include higher alcohols having carbon atoms 8–36 such as, for instance, decyl alcohol, lauryl alcohol, myristyl alcohol, cetyl alcohol, stearyl alcohol, arachidic alcohol, behenyl alcohol, myricyl alcohol, oleyl alcohol, 5,7,7-trimethyl-2-(1′,3′,3′-trimethyl butyl)octanol, 2-ethylhexyl alcohol, 2-hexyldecyl alcohol, 2-heptylundecyl alcohol and 2-octyl dodecyl alcohol.

The straight-chain or branched, higher saturated or unsaturated fatty acids used for the polyglycerol ester type compounds expressed by formula (II) may include higher fatty acids having carbon atoms of 8–36 such as, for example, lauric acid, myristic acid, palmitic acid, stearic acid, oleic acid, behenic acid, cerotic acid, melissic acid, 2-ethylhexanoic acid, 2-hexyldecanoic acid, 2-heptylundecanoic acid, 2-octyldodecanoic acid, 5,7,7-trimethyl-2-(1′,3′,3′-trimethyl butyl)octanoic acid and neodecanoic acid obtained by a reaction between an olefin and carbon monooxide. As the polymethylene oxide use may be made of trimethylene oxide, tetrahydrofuran, etc.

The polyglycerol ether type compounds expressed by formula (I) is synthesized as follows:

A mixture of glycidol with polymethylene oxide is gradually added for polymerization to the aforesaid alcohol or a solution thereof without a solvent or in a solvent such as chloroform or dichloromethane. The polymerization catalyst applied may be Lewis acids such as aluminium chloride, zinc chloride, zinc perchlorate and boron trifluoride-ether complexes. After the completion of reaction, the catalyst is removed with one or more of sodium hydrogen carbonate, sodium carbonate, potassium carbonate, basic alumina and the like. The solvent and unreacted matter are then distilled off under reduced pressure to obtain a viscous, oily or semi-solid product. Alternatively, only glycidol may be added dropwise to trimethylene oxide or tetrahydrofuran serving as a solvent.

The polyglycerol ester type compounds expressed by formula (II) may be synthesized in the manner as explained with reference to the synthesis of the polyglycerol ether type compounds of formula (I), provided that the aforesaid fatty acids are replaced for the alcohols. Another possibility is that a mixture of glycidol with polymethylene oxide is combined with the aforesaid Lewis acid being used as a catalyst, followed by removal of the catalyst and, thereafter, the resulting product is esterified in the conventional manner with or without an alkali catalyst into a viscous, oily or semi-solid product.

Increases or decreases in the content of polymethylene oxide are achieved by increasing or decreasing the amount thereof.

Typical examples of the higher aliphatic alcohol polymethylene oxide polyglycerol ether compounds and the higher fatty acid polymethylene oxide polyglycerol ester compounds of formulae (I) and (II) according to the present invention include:

poly(glycerol)(8)poly(1,4-oxybuthylene)(4)myristyl ether,
poly(glycerol)(14)poly(1,3-oxytrimethylene)(6)cetyl ether,
poly(glycerol)(20)poly(1,4-oxybutylene)(10)stearyl ether,
poly(glycerol)(10)poly(1,4-oxybutylene)(9)stearyl ether,
poly(glycerol)(20)poly(1,3-oxytrimethylene)(20)oleyl ether,
poly(glycerol)(32)poly(1,4-oxybutylene)(32)oleyl ether,
poly(glycerol)(15)poly(1,4-oxybutylene)(14)2-octyldodecyl ether,
poly(glycerol)(5)poly(1,3-oxytrimethylene)(6)palmitate,
poly(glycerol)(5)poly(1,4-oxybutylene)(10)stearate,
poly(glycerol)(6)poly(1,4-oxybutylene)(4)stearate,
poly(glycerol)(30)(1,3-oxytrimethylene)(20)oleate,
poly(glycerol)(20)poly(1,4-oxybutylene)(10)2-hexyldecanaote.

The present invention will now be elucidated with reference to the examples of synthesis of the inventive novel polyglycerol compounds.

SYNTHESIS EXAMPLE 1

Poly(glycerol)(10)poly(1,4-oxybutylene)(9)2-octyldodecyl ether

One (1) gram of a boron trifluoride ether complex was added to 28.5 grams of 2-octyldodecyl alcohol and 150 ml of tetrahydrofuran. 74 grams of glycidol were added dropwise for one hour agitation at 40° C. in a nitrogen stream. After the dropwise addition, the reaction was continued for further 30 minutes to completion. Thereafter, 20 grams of sodium bicarbonate were added to the reaction product which was treated under the same conditions for 4 hours. After filtration of insoluble matters, the solvent and unreacted glycidol were distilled off under reduced pressure to obtain the captioned compound as a colorless oil in a yield of 163 grams.

| ELEMENTAL ANALYSIS as $C_{86}H_{174}O_{30}$ | | |
|---|---|---|
| | Carbon | Hydrogen |
| Calcd. | 61.21% | 10.23% |
| Found | 61.18% | 10.20% |

The NMR of the compound after acetylation is shown in FIG. 1.

SYNTHESIS EXAMPLE 2

Poly(glycerol)(16)poly(1,4-oxybutylene)(12)stearyl ether

One gram of zinc tetrachloride was added to 27 grams of stearyl alcohol and 140 ml of tetrahydrofuran. 119 grams of glycidol were added dropwise under agitation for one hour in a nitrogen stream. After the dropwise addition, the reaction was continued for further 30 minutes to completion. 30 grams of sodium carbonate were added to the reaction product which was then treated under the same conditions for 4 hours. After filtration of insoluble matters, the solvent and unreacted glycidol were distilled off under reduced pressure to obtain the captioned compound as a colorless semi-solid in a yield of 118 grams.

| ELEMENTAL ANALYSIS as $C_{114}H_{130}O_{45}$ | | |
|---|---|---|
| | Carbon | Hydrogen |
| Calcd. | 56.55% | 7.81% |
| Found | 56.59% | 7.71% |

Figure 2:
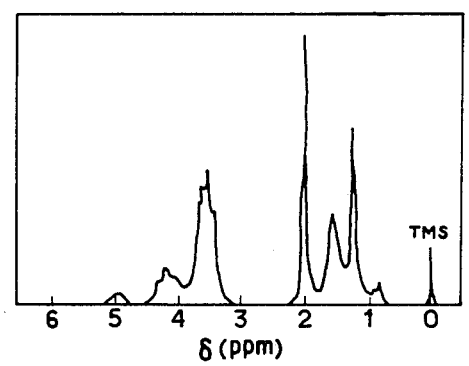

The NMR of the compound after acetylation is shown in FIG. 2.

SYNTHESIS EXAMPLE 3

Poly(glycerol)(32)poly(1,4-oxybutylene)(32)oleyl ether

One gram of a boron trifluoride ether complex was mixed with 27 grams of oleyl alcohol and 100 ml of dichloromethane. Which applying heat, a mixture of 240 grams of glycidol with 200 grams of tetramethylene oxide was added dropwise under agitation and reflux for about 4 hours in a nitrogen stream. After the completion of dropwise addition, the reaction was continued for further two hours. Thereafter, 20 grams of sodium carbonate were added to the reaction product which was then treated under the same conditions for three hours. After filtration of insoluble matters, the solvent and unreacted glycidol were distilled off under reduced pressure to obtain the captioned compound as a colorless semi-solid product in a yield of 450 grams.

| ELEMENTAL ANALYSIS as $C_{210}H_{348}O_{97}$ | | |
|---|---|---|
| | Carbon | Hydrogen |
| Calcd. | 56.55% | 7.81% |
| Found | 56.58% | 7.79% |

Figure 3:
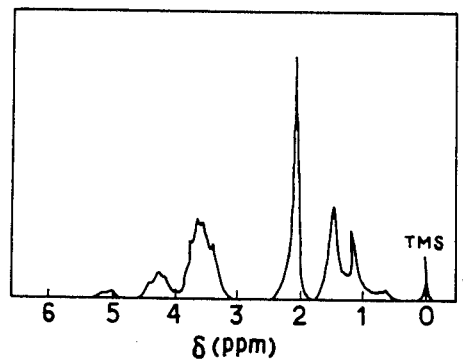

The NMR of the compound after acetylation is shown in FIG. 3.

SYNTHESIS EXAMPLE 4

Poly(glycerol)(6)poly(1,3-oxytrimethylene)(4)2-heptylundecanoate

One gram of a boron trifluoride ether compolex was mixed with 28.4 grams of 2-heptylundecanoic acid and 100 ml of dichloromethane. A mixture of 45 grams of glycidol and 23.2 grams of trimethylene oxide was added dropwise to the obtained mixture for 4 hours under stirring and reflux in a nitrogen stream. After the addition, the reaction was continued for further two hours. Thereafter, 30 grams of potassium carbonate were added to the reaction product which was in turn treated under the same conditions for 4 hours. After filtration of insoluble matters, the solvent and unreacted glycidol were distilled off under reduced pressure to obtain the captioned compound as a colorless oil in a yield of 93 grams.

| ELEMENTAL ANALYSIS as $C_{48}H_{98}O_{17}$ | | |
| --- | --- | --- |
| | Carbon | Hydrogen |
| Calcd. | 60.89% | 10.36% |
| Found | 60.77% | 10.39% |

SYNTHESIS EXAMPLE 5

Poly(glycerol)(10)poly(1,3-oxytrimethylene)(8)stearate

One gram of a boron trifluoride ether complex was mixed with 9 grams of glycerol and 120 ml of dichloromethane. To the obtained mixture was added dropwise a mixture of 72 grams of glycidol and 47 grams of trimethylene oxide for 4 hours under agitation and reflux in a nitrogen stream. After the addition, the reaction was continued for further one hour. Thereafter, 20 grams of sodium bicarbonate were added to the reaction product which was then treated under the same conditions for 4 hours. After filtration of insoluble matters, the solvent and unreacted glycidol were distilled off under reduced pressure to obtain a mixture. 28 grams of stearic acid were added to the mixture at 230° C. for 4 hours. Removal of water gave the captioned compound as a colorless semisolid product in a yield of 114 grams.

| ELEMENTAL ANALYSIS as $C_{72}H_{144}O_{30}$ | | |
| --- | --- | --- |
| | Carbon | Hydrogen |
| Calcd. | 58.06% | 9.68% |
| Found | 57.92% | 9.70% |

The thus obtained poly(glycerol)poly(oxypolymethylene)alkyl ehters and the poly(glycerol)poly(oxypolymethylene) fatty acid esters that are novel polyglycerol compounds may be used alone or in combination and, optionally, with nonionic surfactants having no ethylene oxide chain such as sorbitan monostearate and glycerol monooleate having a HLB of not greater than 7, as an emulsifier.

The characteristic features of the emulsifer according to the present invention are that it has no ethylene oxide chain in its molecule and no 1,2-bonding in its polymethylene oxide groups. For this reason, the emulsifier undergoes little or no elution of formaldehyde and pH changes due to oxidation, so that considerable improvements are introduced in safety and stability. Because of its odorless, the inventive emulsifier helps reduce the chances of giving off an offensive smell. The inventive emulsifier also limits the adsorption of paraben compounds onto a surface active agent, and helps reduce the amount of antiseptics used.

To prove the feature of the inventive polyglycerol compounds according to which they can be used as emulsifiers, the following experiments were performed.

(1) Testing on Elution of Formaldehyde

Figure 4:
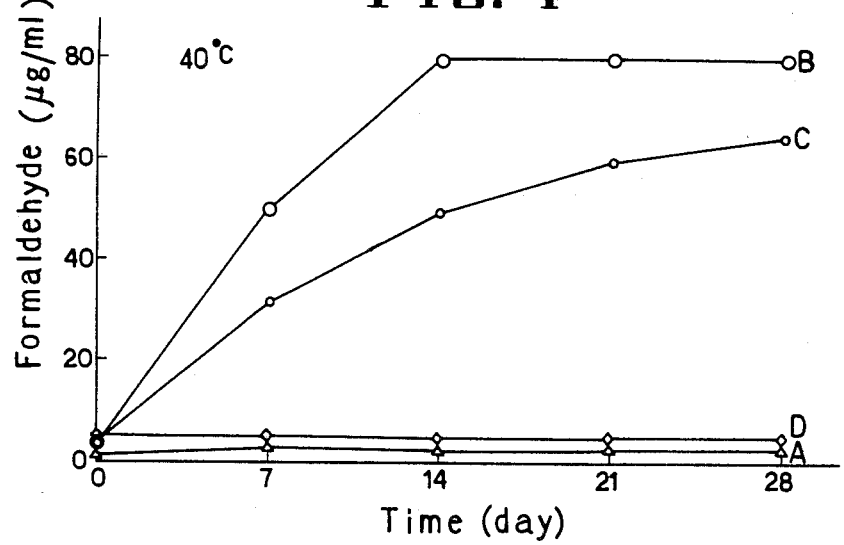
FIGS. 4 and 5 are graphical views showing the results of testing on the amount of elution of formaldehyde and pH changes of an aqueous solution of nonionic surfactants, wherein A is poly(glycerol)(10)poly(1,3-oxytrimethylene)(8)-stearate,
B is poly(oxyethylene)(20)sorbitan monostearate,
C is poly(oxyethylene)(20)sorbitan monooleate, and
D is poly(glycerol)(16)poly(1,4-oxybutylene)(12)stearyl ether.

Prepared were the novel emulsifying compounds according to the present invention [poly(glycerol)(10-)poly(1,3-oxytrimethylene)(8)stearate and poly(glycerol)(16)poly(1,4-oxybutylene)(12)stearyl ether] and the known hydrophilic, nonionic surface active agents [poly(oxyethylene)sorbitan monooleate and poly(oxyethylene)sorbitan monostearate] in the form of 1% aqueous solutions. These solutions were allowed to stand for one month at 40° C. to determine the amount of formaldehyde by means of the acetyl acetone method. FIG. 4 shows the results, from which it is evident that the inventive products undergo little or no elution of formaldehyde even under a severe temperature condition of as high as 40° C.

(2) Testing on pH changes

Figure 5:
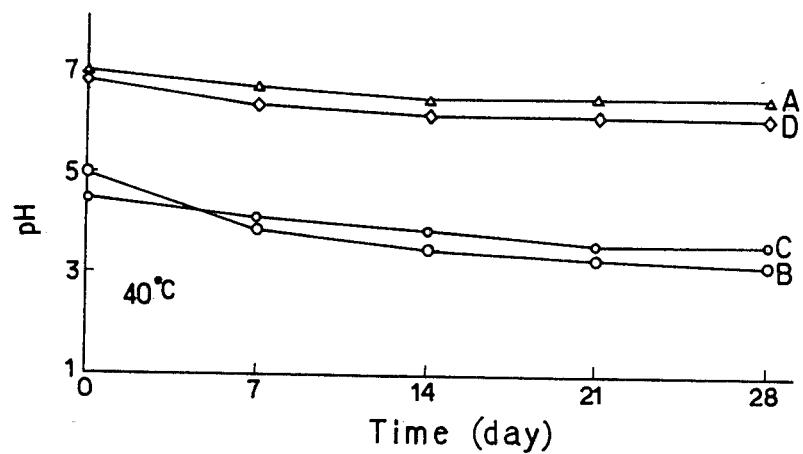

Prepared were the novel polyglycerol compounds [poly(glycerol)(16)poly(1,4-oxybutylene)(12)stearyl ether and poly(glycerol)(10)poly(1,3-trimethylene)(8)-stearate] and the known hydrophilic, nonionic surface active agents [poly(oxyethylene)(20)sorbitan monostearate and poly(oxyethylene)(20)sorbitan monooleate] in the form of 1% aqueous solutions. These solutions were allowed to stand for one month at 40° C. to determine changes in pH. FIG. 5 shows the results, from which it is evident that the inventive products are less than the known surfactants in the changes in pH.

These results are attributable to the fact that the novel compounds of the present invention have no 1,2-bonding in the polymethylene oxide groups. The surface active agents yet used in the art are prone to decomposition due to pH changes caused by the oxidation thereof. However, the inventive compounds do hardly show any sign of decomposition. Especially with a system wherein pharmaceutically active components are present such as various derivatives of ascrobic acid and glutathione, the decomposition of such active components is promoted according as the surfactant is oxidized. However, such a disadvantage is eliminated or reduced by the present invention.

Another aspect of the present invention will now be explained, according to which the inventive polyglycerol ether type compounds can be made more suitable for use in cosmetic emulsifiers.

Since the compounds of the present invention are available in the form of non-crystalline (semi-)solids, they can provide a creamy semi-solid emulsion which remains substantially intact in a low to high temperature region. As compared with this, the known emulsifiers such as poly(oxyethylene)(10)stearyl ether exhibit so high a crystallinity that there is a sharp change in hardness in the vicinity of their melting point of 40° C. It is thus likely that the emulsions may solidify at lower temperatures and flow at higher temperatures. Furthermore, the prior art poly(oxyethylene)sorbitan monostearate has so low a melting point that no cream having a sufficient hardness is obtained.

As explained above, the polyglycerol compounds of the present invention provide an ideal emulsifying system for cosmetics which shows a lower crystallinity as compared with the conventional polyethylene oxide, is highly stable to temperature and oxidation, and has its hardness varying to only a limited degree.

In general, cosmetics include antiseptics such as represented by paraben compounds for the purpose of preventing secondary contamination. Reportedly, the paraben compounds are less effective in an emulsifying system, since they are adsorbed onto the ethylene oxide chain of the surface active agent. With the inventive compounds, however, such deactivation is considered not to take place due to the absence of any ethylene oxide chain. To prove this, testing was carried out with emollient cream of Example 1 (O/W emulsion) containing as the emulsifier 5% by weight of poly(glycerol)(10-

)poly(1,4-oxybutylene)(9)stearyl ether of the present invention and 0.3% by weight of parabens (a mixture of methylparaben and butylparaben) and control emollient cream containing as the emulsifier the same amount of the prior art sorbitan monostearate and poly(oxyethylene)(20)sorbitan monostearate and the same amount of the parabens. In that testing, a difference in aseptic effect between both samples was determined with several mold and bacteria. The results are shown in Table 1.

TABLE 1

Testing on Aspetic Effect

| Samples under testing | Bacteria under testing | | | | | | | | | | | | |
|---|---|---|---|---|---|---|---|---|---|---|---|---|---|
| | Staphylococcus aureus + Escherichia coli | | | | Aspergillus niger + Penicillium citrinum | | | | Pseudomonas aerunginosa | | | | |
| | days | | | | | | | | | | | | |
| | 0 | 1 | 2 | 4 | 7 | 0 | 1 | 2 | 4 | 7 | 0 | 1 | 2 | 5 | 7 |
| Ex. 1 (present invention) | | | ± | – | | | | | + · | | + | – | – | – |
| Control cream | | | | + | | | | | | | | + | – | – |

| Samples testing | Bacteria under testing | | | | | | | | | | | | |
|---|---|---|---|---|---|---|---|---|---|---|---|---|---|
| | Bacillus subtiles | | | | Candida albicans | | | | Aerobacter aerogenes | | | | |
| | days | | | | | | | | | | | | |
| | 0 | 1 | 2 | 5 | 7 | 0 | 1 | 2 | 5 | 7 | 0 | 1 | 2 | 5 | 7 |
| Ex. 1 | | – | – | – | | | – | – | – | – | | ± | – | – |
| Control cream | | – | – | – | · | | + | ± | – | – | | + | ± | |

Number of Colonies — 0
± 1–4
+ 5–below 200
200–below 1000
1000–below 10⁴

From Table 1, it has been found that the emulsion system according to the present invention is superior in aseptic effect to the poly(oxyethylene)sorbitan base system. It has already been reported in The 34th Colloid and Interface Chemistry Symposium in Japan the intensity of fluorescence is increased upon the adsorption of parabens onto surfactants. Measurements were therefore made of the intensity of fluorescence 4 ppm methylparaben aqueous solutions in which dissolved were the same amount of the inventive polyglycerol base surface [poly(glycerol(15)poly(1,4-oxybutylene)(14)2-octyldodecyl ether] and the conventional polyethylene oxide base surfactant (Nikkol HCO-50, manufactured by Nikko Chemical K.K.) with the use of a fluorimeter type RF510 manufactured by Shimazu Seisakusho K.K. As a result, it has turned out that the intensity of fluorescence of the aqueous solution of the polyglycerol base surfactant is lower than that of the polyethylene oxide base surfactant. This means that the adsorption of parabens is so less that a smaller amount of antiseptics gives rise to the same effect.

Figure 6:
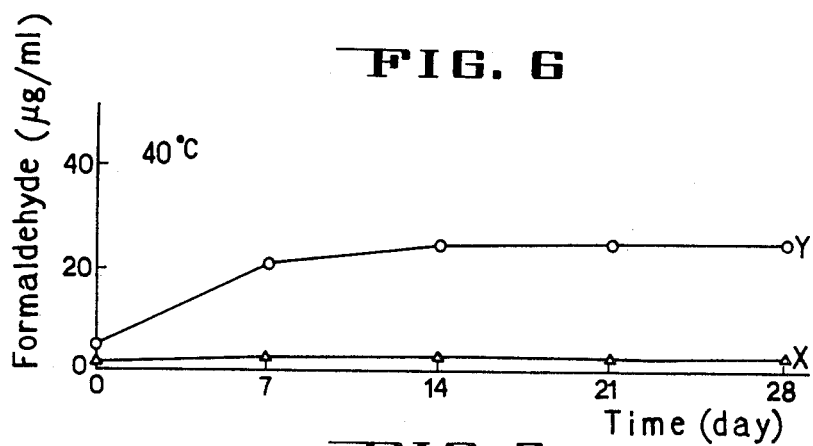
FIGS. 6 and 7 are graphical views showing the results of testing on the amount of elution of formaldehyde and pH changes of an aqueous solution of solubilizers, wherein X is poly(glycerol)(16)poly(1,4-oxybutylene)(8)2-octyldodecyl ether, and
Y is hydrogenated castor oil poly(oxyethylene)(40) adduct.
Figure 7:
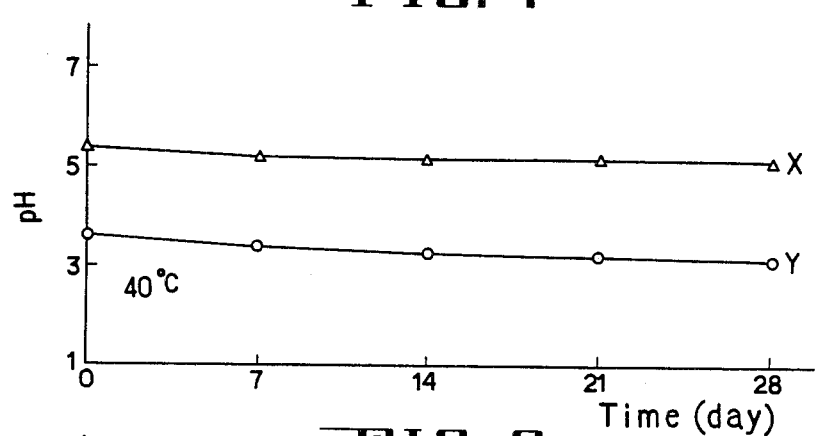

Reference will now be made to the possibility of application of the inventive polyglycerol ether type compound to solubilizers. The poly(glycerol)poly(oxypolymethylene) branched fatty alcohol ehters expressed by formula (I) are Micelle-dissolved in water, and solubilize perfumes and oily matters. The characteristic feature of the solubilizers of the present invention is the absence of an ethylene oxide. Like the foregoing emulsifiers, therefore, the solubilizers causes little or no elution of formaldehyde and pH changes, and are colorless as well as odorless. The inventive solubilizer poly(glycerol)(16)poly(1,4-oxybutylene)(8)2-octydodecyl ether and the known solubilizer [hydrogenated castor oil poly(oxyethylene)(40) adduct] were prepared in the form of 1% aqueous solutions to determine the amount of elution of formaldehyde and pH changes in the same manner as described in connection with the aforesaid emulsifier. The results are set forth in FIGS. 6 and 7 and obviously indicate that the inventive solubilizer shows lesser signs of elution of formaldehyde and pH changes as compared with the known hydrogenated castor oil poly(oxyethylene) adduct that is said to be not noticeably varied among the nonionic surface active agents.

Still another feature of the present invention is that the compound of formula (I) may be used as a solubilizer for cosmetics, when it is a poly(glycerol) branched alkyl ether.

Most of the known nonionic surface active agents have their alkyl nuclears including a relatively short chain length or a double bond. This is because, in the case of long-chain alkyl groups, pearl-like crystals precipitate resulting from the Krafft points of the nonionic surface active agents, and lead to instability of the products. With the inventive solubilizers, there is no possibility of precipitation of crystals since they are based on polyglycerol and have a low melting point. In addition, it is also possible to obtain a solubilizing system even with the use of an alcohol with its straight-chain or branched alkyl being long, thus allowing product design that is more safe and more stable to oxidation.

Figure 8:
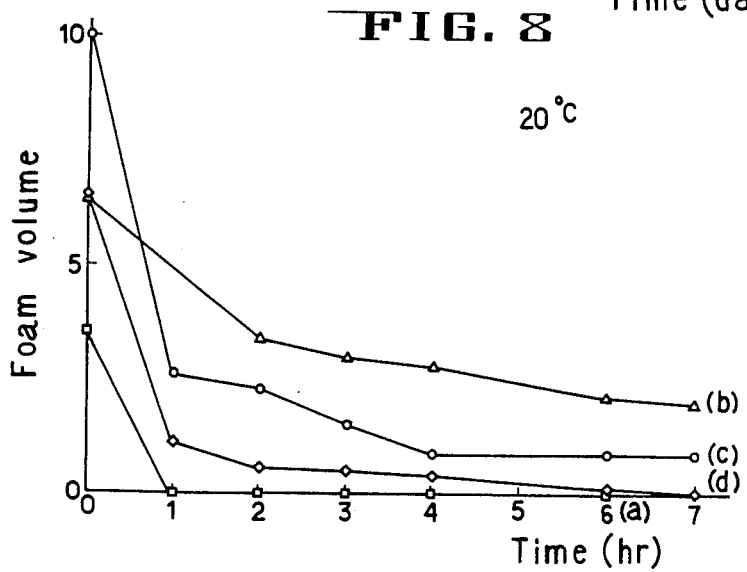
FIG. 8 is a graphical view showing changes on the volume of bubbles with the lapse of time observes on solubilized type lotion after shaking, wherein (a) is poly(glycerol)(15)poly(1,4-oxybutylene)(14)2-octyldodecyl ether,
(b) is poly(oxyethylene)(30)2-hexyldecanoate
(c) is poly(oxyethylene)(20)oleyl ether, and
(d) is hydrogenated castor oil poly(oxyethylene)50) adduct

The solubilized type lotion generally has a bubbling tendency and, once bubbled, bubbles continue to be present over a considerable period of time. It is said in view of both appearance and touch during hand-spreading that the less the bubbles, the better the quality would be. The inventive solubilizer is characterized by its fast rate at which bubbles break (hereinafter referred to as the defoaming rate). To substantiate this, a lotion sample in which perfumes are solubilized by poly(glycerol)(15)poly(1,4-oxybutylene)(14)-2-octyldodecyl ether and a control lotion sample in which the perfumes are solubilized by the known solubilizers [three kinds of poly(oxyethylene) base surfactants] were prepared to observe their defoaming state at 20° C. The lotion samples were charged into 30 ml-test tubes in amounts of 10 ml, and vigorously shaken 50 times in the vertical direction. The volume of bubbles was measured with the lapse of time to determine the amount of the remaining bubbles. FIG. 8 indicates that the hydrogenated castor oil poly(oxyethylene) adduct contributes to a faster defoaming rate among the known nonionic surfactants, poly(oxyethylene)(30)2-hexyldecanoate poly(oxyethylene)(20)oleyl ether and hydrogenated castor oil poly(oxyethylene)(50) adduct, and the inventive solubilizer is by far superior in the defoaming rate to that adduct.

The solubility of surfactants depends largely upon HLB. The optimum HLB for solubilization is taken as being 12-15. The substances to be applied over the skin of human beings, such as cosmetics, should be safe as much as possible. It is said that increases in molecular weight would be effective for safety. Increases in the molecular weight of nonionic surfactants may be achieved by increasing the number of moles of the hydrophilic groups added; however, too high a molecular weight causes that HLB may exceed the upper limit of the optimum range for solubilization.

With the inventive solubilizer, it is possible to increase only the molecular weight, while keeping the HLB constant in the desired range. This is because the inventive solubilizer includes a group allowing the HLB to shift to the lipophilic side, such as 1,4-butylene oxide.

The polyglycerol ether type compounds of the present invention, whether used as emulsifiers or solubilizers, can provide surface active agents which are safer than ever in view of stimulation to the skin.

To substantiate this, simple emulsions comprising liquid paraffin-water were prepared as samples, which contained 20% by weight of the inventive compounds [poly(glycerol)(16)poly(1,4-oxybutylene)(10)2-octyldodecyl ether and poly(glycerol)(16)poly(1,4-oxybutylene)(10)stearyl ether] and the known sorbitan base, nonionic surfactants poly(oxyethylene)(20)sorbitan monostearate. The thus obtained emulsion samples are applied over the skin of rabbits to try primary irritation testing (percutaneous) for the comparison of difference in irritation.

In the testing, a total of 0.3 ml of the samples were administered to Angora rabbits in three equal doses at an interval of 24 hours. Four days after administration, estimations were made of irritation to the skin. Table 2 shows the results, from which it has been found that the irritating action the inventive compounds have is equivalent to, or less than, that of the sorbitan fatty acid esters which are said to be relatively safer. This implies that the inventive compounds are proved to be satisfactorily safe for use.

surface active agents exceling in safety and stability, and added to a variety of cosmetics in the required amounts depending upon the kinds thereof. For instance, it is preferable that the inventive compounds are used as solubilizers for lotion products in an amount ranging from 0.1 to 10% by weight, and as emulsifiers for cream products, etc., in an amount ranging from 0.5 to 60% by weight.

Functioning as surface active agents, the inventive compounds may find use in various applications inclusive of detergents, soaps and pharmaceutics.

The solubilization of the inventive polyglycerol compounds and the cosmetic products containing them will now be explained with reference to the following, non-restrictive examples wherein the proportion of components is indicated by percentage by weight.

EXAMPLE 1

Emollient Cream

| | | |
|---|---|---|
| (1) | Poly(glycerol)(10)poly(1,4-oxybutylene)(9)stearyl ether | 3.0 |
| | Poly(glycerol)(4)poly(1,4-oxybutylene)(4)stearyl ether | 2.0 |
| | Stearic acid | 5.0 |
| | Cetyl alcohol | 3.0 |
| | Squalane | 10.0 |
| | Bees wax | 2.0 |
| | Spermaceti | 1.0 |
| | Lanolin | 2.0 |
| | Parabens (mixture of methylparaben and butylparaben) | 0.3 |
| | Perfumes | 0.3 |
| (2) | Propylene glycol | 7.0 |
| | Glycerol | 4.0 |
| | Refined water | 61.0 |

(1) and (2) were heated to 70° C. (2) was added under stirring to (1). After the completion of reaction, the reaction product was uniformly emulsified in a homomixer, and cooled down to 30° C. in a heat exchanger.

EXAMPLE 2

Emollient Lotion

| | | |
|---|---|---|
| (1) | Poly(glycerol)(6)poly(1,3-oxytrimethylene)(5)stearate | 3.0 |
| | Stearic acid | 2.0 |
| | Cetyl alcohol | 1.5 |
| | Lanolin | 2.0 |
| | Squalane | 10.0 |
| | Antiseptics | given amount |
| | Perfumes | " |
| (2) | Propylene glycol | 4.0 |
| | Sorbitol | 4.0 |

TABLE 2

| | Sample | | |
|---|---|---|---|
| | Invention Emulsion | | |
| Type of test | Poly (glycerol) (16) Poly (1,4-oxybutylene) (10) 2-octyldodecyl ether | Poly (glycerol) (16) (1,4-oxybutylene) (10) Stearyl ether | Conventional Emulsion Using poly (oxyethylene) (20) sorbitan monostearate |
| Erythema | 0.30 | 0.40 | 0.39 |
| Vasodilation | 0.43 | 0.94 | 1.11 |
| Edema | 0.41 | 0.60 | 0.48 |
| ICP* | 0.01 | 0.01 | 0.01 |
| Total | 1.14 | 1.95 | 1.99 |

Primary irritation test (percutaneous) with Angora rabbit - After 4 days
For estimation, a range of 0 (no irritation) to 3.0 (strong irritation) is divided into 20 grades. The results are given by the average of 20 measurements
*(Increased Capillary Permeability by Evans Blue Method)

As described above, the polyglycerol ether compounds of the present invention can provide nonionic

| | |
|---|---|
| Carboxyvinyl polymer | 0.1 |
| Refined water | 63.4 |

| | |
|---|---|
| (3) 10% aqueous solution of triethanolamine | 10.0 |

(1) and (2) were heated to 70° C. (2) was added under stirring to (2). After the completion of reaction, the reaction product was uniformly emusified in a homomixer. (3) was slowly added under agitation to the emulsion for neutralization. Thus obtained product was cooled down to 30° C. in a heat exchanger.

EXAMPLE 3

Creamy Foundation

| | | |
|---|---|---|
| (1) | Poly(glycerol)(5)poly(1,4-oxybutylene)(6)palmitate | 3.0 |
| | Stearic acid | 4.0 |
| | Glycerol monostearate | 3.0 |
| | Cetyl alcohol | 1.0 |
| | Liquid paraffin | 7.0 |
| | Glycerol tris-2-ethyl hexanoate | 7.0 |
| | Antiseptics | given amount |
| (2) | Refined water | 55.0 |
| | Triethanolamine | 1.0 |
| | Sorbitol | 3.0 |
| (3) | Titanium oxide | 8.0 |
| | Kaolin | 5.0 |
| | Talc | 2.0 |
| | Bentonite | 1.0 |
| | Coloring pigments | given amount |
| (4) | Perfumes | " |

Pigments (3) were mixed together and pulverized. (3) was dispersed in aqueous phase (2) heated to 80° C. (1) was solubilized by heating to 80° C., and gradually added to (2) for emulsification. The emulsion was cooled under stirring, and added with (4), followed by cooling down to 30° C.

EXAMPLE 4

Lotion

| | | |
|---|---|---|
| (1) | Poly(glycerol)(15)poly(1,4-oxybutylene)(14)-2-octyldodecyl ether | 1.0 |
| (2) | Perfumes | 0.4 |
| (3) | 1,3-butylene glycol | 2.5 |
| (4) | Sorbitol | 2.5 |
| (5) | Ethanol | 5.0 |
| (6) | Distilled water | 89.4 |

| | |
|---|---|
| (7) Methylparaben | given amount |

At room temperature (6) was added under agitation to a solution obtained by solubilization of (1), (2), (3) and (7), followed by further addition of (4) and (5).

EXAMPLE 5

Solubilization of Jojoba Oil

| | | |
|---|---|---|
| (1) | Poly(glycerol)(16)poly(1,4-oxybutylene)(8)2-hexyldecyl ether | 1.0 |
| (2) | Jojoba oil | 0.3 |
| (3) | Perfumes | 0.4 |
| (4) | 1,3-butylene glycol | 5.0 |
| (5) | Distilled water | 68.3 |
| (6) | Ethanol | 5.0 |
| (7) | Antiseptics | given amount |

At room temperature (5) was added under stirring to a uniform solution of (1)–(4) and (7), followed by further addition of (6).

What is claimed is:

1. A polyglycerol compound expressed by the following Formula (I) or (II):

$$R_1O(X_1)m_1-Y_1-_{n1}H \quad (I)$$

wherein $R_1$ is a straight-chain or branched saturated or unsaturated aliphatic alcohol residue having carbon atoms of 8–36, $X_1$ is $CH_2CH_2CH_2O$ and/or $CH_2CH_2CH_2CH_2O$, $Y_1$ is a glycerol residue, $X_1$ and $Y_1$ are randomly arranged, $m_1$ equals 3–60, and $n_1$ equals 4–60, or $$R_2COO(X_2)m_2-Y_2-_{n2}H \quad (II)$$

wherein $R_2$ is a straight-chain or branched, saturated or unsaturated fatty acid residue having carbon atoms of 7–35, $X_2$ is $CH_2CH_2CH_2O$ and/or $CH_2CH_2CH_2CH_2O$, $Y_2$ is a glycerol group, $X_2$ and $Y_2$ are randomly arranged, $m_2$ equals 3–60, and $n_2$ equals 4–60.

2. The compound of claim 1 wherein $m_1$ and $m_2$ each equals 4–60 and $n_1$ and $n_2$ each equals 5–30.

3. The compound of claim 1 wherein the ratio of $m_1$ to $n_1$ and of $m_2$ to $n_2$ is each within the range of 95:5–1:3.

4. The compound of claim 3 wherein the ratio of $m_1$ to $n_1$ and of $m_2$ to $n_2$ is each within the range of about 1:1–2:1.

* * * * *